(12) United States Patent
Itzhak et al.

(10) Patent No.: US 8,398,917 B2
(45) Date of Patent: Mar. 19, 2013

(54) METHOD AND APPARATUS FOR TREATING BIOLOGICALLY CONTAMINATED AIR

(75) Inventors: Ron Itzhak, Tel-Aviv (IL); David Itzhak, Tel-Aviv (IL)

(73) Assignee: Megair Ltd., Rishon le-Zion (IL)

( * ) Notice: Subject to any disclaimer, the term of this patent is extended or adjusted under 35 U.S.C. 154(b) by 815 days.

(21) Appl. No.: 12/073,173

(22) Filed: Feb. 29, 2008

(65) Prior Publication Data

US 2010/0043632 A1 Feb. 25, 2010

Related U.S. Application Data

(63) Continuation-in-part of application No. PCT/IL2006/001010, filed on Aug. 31, 2006.

(30) Foreign Application Priority Data

Sep. 1, 2005 (IL) .......................................... 170605

(51) Int. Cl.
*A61L 9/00* (2006.01)

(52) U.S. Cl. .................. 422/4; 95/149; 96/234; 422/31; 422/123

(58) Field of Classification Search ............. 95/92, 149, 95/187, 191, 207, 64–65; 96/19; 426/235
See application file for complete search history.

(56) References Cited

U.S. PATENT DOCUMENTS

| | | | | |
|---|---|---|---|---|
| 2,967,807 | A | * | 1/1961 | Miller et al. .................. 205/524 |
| 3,220,942 | A | * | 11/1965 | Crites ............................ 205/731 |
| 3,339,475 | A | | 9/1967 | Martin |
| 3,475,122 | A | * | 10/1969 | McRae et al. ................. 423/539 |
| 3,801,698 | A | * | 4/1974 | Lowrance et al. ............. 423/234 |
| 3,819,329 | A | * | 6/1974 | Kaestner et al. .................... 422/3 |
| 4,057,473 | A | * | 11/1977 | Cunningham et al. ......... 205/347 |
| 4,069,117 | A | * | 1/1978 | Cooper .......................... 423/220 |
| 4,343,765 | A | | 8/1982 | Elston et al. |
| 4,685,617 | A | * | 8/1987 | Assaf .............................. 237/81 |
| 4,748,904 | A | | 6/1988 | Razeto et al. |
| 4,872,315 | A | | 10/1989 | Assaf |
| 5,009,869 | A | * | 4/1991 | Weinberg et al. ............. 423/210 |

(Continued)

FOREIGN PATENT DOCUMENTS

EP 0 230 875 B1 8/1987
EP WO 94/11091 5/1994

(Continued)

OTHER PUBLICATIONS

International Search Report for PCT/IL2006/001010 dated Apr. 2, 2007.

(Continued)

*Primary Examiner* — Duane Smith
*Assistant Examiner* — Ives Wu
(74) *Attorney, Agent, or Firm* — Nixon & Vanderhye P.C.

(57) ABSTRACT

A method for reducing biological contamination of indoor air, which method includes providing a concentrated salt solution, which is either (i) a brine capable of responding to aeration thereof by a rapid increase of its Redox potential, wherein the rate of said increase is greater than the rate of increase observed for a 45% (w/w) calcium chloride solution subjected to identical aeration conditions; or (ii) a brine which is passed through an electrolytic cell in order to raise its Redox potential; circulating said concentrated salt solution through a treatment zone; causing a stream of biologically contaminated air to flow through said treatment zone, such that said contaminated air is contacted with said salt solution in said treatment zone; and withdrawing purified air from said treatment zone.

22 Claims, 10 Drawing Sheets

U.S. PATENT DOCUMENTS

| | | | |
|---|---|---|---|
| 5,688,385 A | 11/1997 | Rhees et al. | |
| 5,792,369 A | 8/1998 | Johnson | |
| 5,866,000 A * | 2/1999 | Yeh | 210/295 |
| 5,902,619 A * | 5/1999 | Rubow et al. | 426/235 |
| 6,296,744 B1 * | 10/2001 | Djeiranishvili et al. | 204/263 |
| 6,843,835 B2 * | 1/2005 | Fornai et al. | 96/53 |
| 6,902,653 B2 * | 6/2005 | Carmignani et al. | 210/748.11 |
| 7,066,884 B2 * | 6/2006 | Custer et al. | 600/309 |
| 7,866,638 B2 * | 1/2011 | Neumann et al. | 261/115 |
| 2002/0056285 A1 | 5/2002 | Elich | |
| 2002/0098128 A1 | 7/2002 | Smith | |
| 2003/0164309 A1 * | 9/2003 | Nakamura et al. | 205/746 |
| 2004/0231512 A1 | 11/2004 | Slayzak et al. | |
| 2004/0261952 A1 | 12/2004 | Hart et al. | |
| 2004/0261958 A1 | 12/2004 | Sugiyama et al. | |
| 2007/0108064 A1 * | 5/2007 | Buckley et al. | 205/620 |
| 2007/0134127 A1 * | 6/2007 | Smith et al. | 422/37 |
| 2007/0148256 A1 | 6/2007 | Yanagihara et al. | |
| 2010/0043632 A1 | 2/2010 | Itzhak et al. | |

FOREIGN PATENT DOCUMENTS

| | | |
|---|---|---|
| JP | 2004-089770 | 3/2004 |
| WO | WO 96/16555 | 6/1996 |
| WO | WO 2006/097634 | 9/1996 |
| WO | WO 00/24431 | 5/2000 |
| WO | 01/78868 | 10/2001 |
| WO | WO 2004/027116 | 4/2004 |
| WO | WO 2007/026363 | 3/2007 |
| WO | WO 2009/107138 | 9/2009 |

OTHER PUBLICATIONS

Silvia D. Stan et al., "Investigation of the Presence of OH Radicals in Electrolyzed NaCl Solution by Electron Spin Resonance Spectroscopy", Journal of Agricultural and Food Chemistry [online], vol. 53., No. 12, 2005, pp. 4901-4905.

L. Øvreås et al, "Characterization of Microbial Diversity in Hypersaline Environments by Melting Profiles and Reassociation Kinetics in Combination with Terminal Restriction Fragment Length Polymorphism (T-RFLP)", Microb Ecol (2003), 46:291-301.

United States Official Action issued for related U.S. Appl. No. 12/735,924, dated Apr. 11, 2012.

International Search Report issued for PCT/IL2009/000227, mailed Jul. 8, 2009.

Written Opinion issued for PCT/IL2009/000227, mailed Jul. 8, 2009.

* cited by examiner

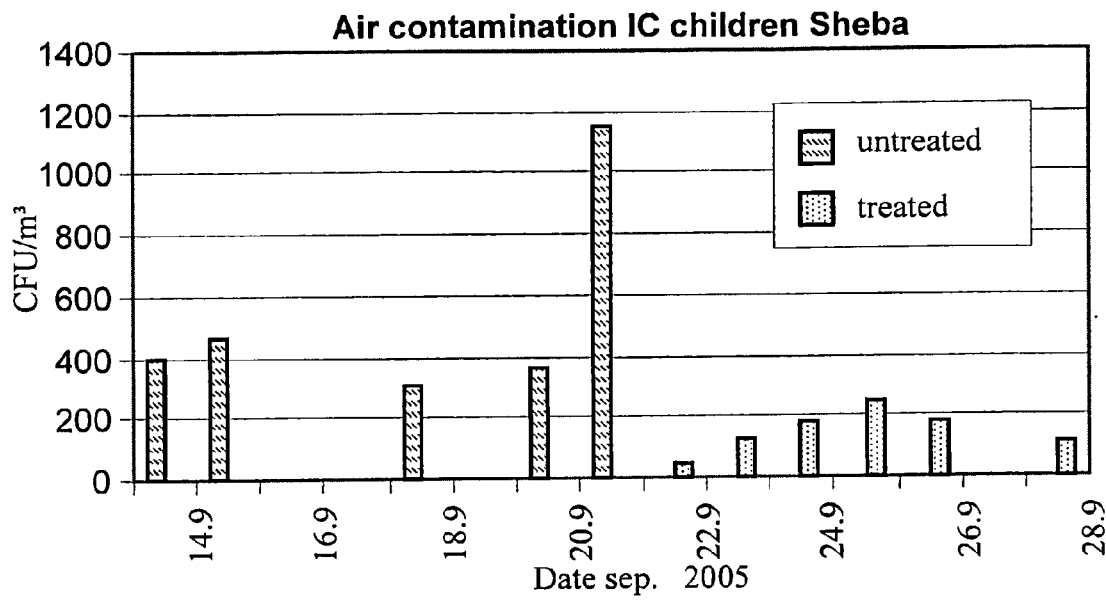
Fig. 14
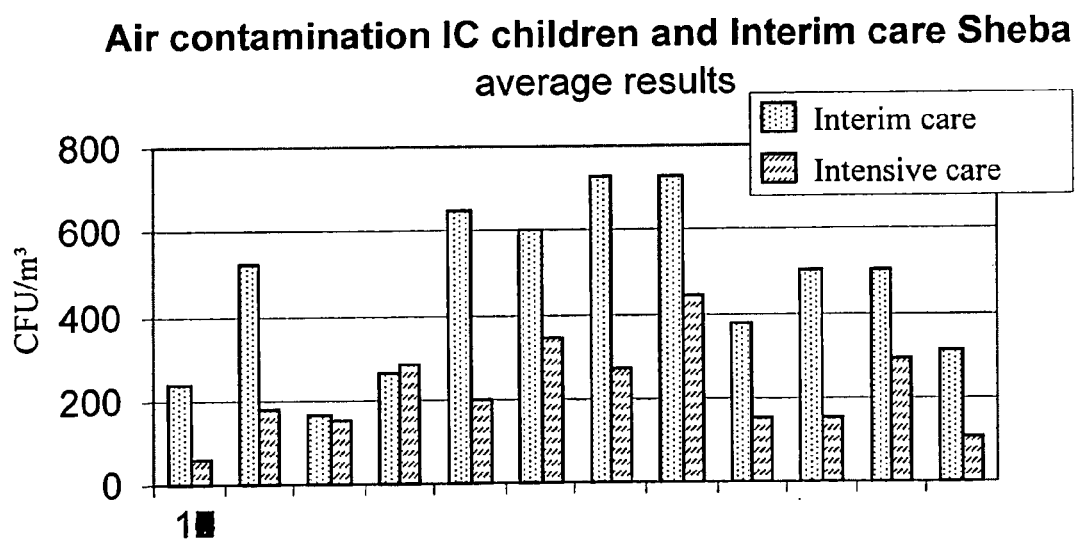
Fig. 15  Twice a day analysis

METHOD AND APPARATUS FOR TREATING BIOLOGICALLY CONTAMINATED AIR

CROSS-REFERENCE TO RELATED APPLICATIONS

This application is a continuation-in-part of International Application No. PCT/IL2006/001010, filed 31 Aug. 2006, which designated the U.S., and claims priority to Israel Application No. 170605, filed 1 Sep. 2005, the entire contents of each of which are hereby incorporated by reference.

Commonly used methods for treating contaminated air include various types of filtration, air ionization and sterilization of air utilizing ozone or ultraviolet light as disinfectants.

Air filters, such as activated carbon filters and High Efficiency Particulate Air (HEPA) filters, are used to remove various chemicals, odors and dust from a stream of air passing therethrough.

Air ionization involves the generation of electrically charged ions in the air. The negatively charged ions become attached to floating particles, which eventually fall out of the air.

Ozone-based purifiers involve the formation of ozone molecules by generating a high-voltage electrical discharge through air or oxygen, or by using some types of ultraviolet lamps. Ozone is known as an excellent oxidizing agent and bactericide.

Ultraviolet (UV) air purifiers are based on the disinfecting properties of UV light. These purifiers contain lamps which generate UV light capable of destroying germs, viruses and bacteria.

Some of the purification systems used today combine several of the above indicated methods to effectively remove particulates and destroy microbial contaminants. For example, in a commercially available apparatus "XJ-3000 C" of Heaven Fresh Canada Inc (http://www.heavenfresh.ca/catalog/), the purification of air is accomplished utilizing: i) air ionization; ii) HEPA air filtration; iii) germicidal UV lamp; iv) an activated carbon filter; v) ozone purification (optional); and vi) anti-bacterial pre-filter for removing large particles (for prolonging the efficiency of the carbon and HEPA filters).

It may be appreciated that among the various types of contaminated air that needs to be treated and purified, indoor air in hospitals, requires a special attention. Common measures currently used for preventing, or at least reducing, the spread of infections in health care facilities include Heating, Ventilating and Air Conditioning (HVAC) maintenance and cleaning, increased ventilation, Ultraviolet Germicidal Irradiation (UVGI), and air filtration. Ideally, a successful treatment of indoor air in hospitals should bring a significant decrease in the level of microbiological load in large volumes of air using inexpensive means.

EP 0230875 describes a process for treating a contaminated air using a filter provided with layers that contain alkaline and acidic agents.

WO 01/78868 describes a process for purifying air by passing a stream of air over rough surfaces covered with salt micro-crystallized sedimentation.

L. Øvreås et al. ["*Characterization of microbial diversity in hypersaline environments by melting profiles and reassociation kinetics in combination with terminal restriction fragment length polymorphism(T-RFLP)*", Microb Ecol. 2003 October; 46 (3):291-301. Epub 2003 Aug. 14] report that the total genetic diversity of prokaryotic communities at different salinities (22, 32, and 37%) were increased from 22% to 32% salinity and were reduced at 37% salinity to nearly half that at 22% salinity.

US 2004/0231512 describes a method and a device for conditioning air and purifying the same by contacting the air with a liquid desiccant (and specifically, a solution of lithium chloride, lithium bromide or calcium chloride), which are commonly used in air conditioning systems as dehumidifiers. The liquid desiccant is subsequently regenerated by heating the same.

It has now been found that certain brines, which are capable of responding to a passage of air therethrough by a rapid and significant increase of their Redox (RedOx—Reduction Oxidation) potential, may be effectively used for reducing considerably the level of biological contaminates present in an indoor air, upon being contacted with the contaminated air. More specifically, it has been observed that the Redox potential of certain brines is rapidly and significantly raised after the brine has been adequately contacted and mixed with the stream of air to be purified, following which the resulting brine becomes a powerful disinfectant.

It has now also been found that oxidant brines, which in the context of the present invention are brines that are periodically passed through an electrolytic cell in order to increase their Redox potential, may also be effectively used in the purification of biologically contaminated air.

Accordingly, the purity and quality of indoor air that it is suspected of being biologically contaminated (e.g., interior hospital air), may be significantly improved following treatment with certain concentrated brines or with oxidant brines.

In a first aspect, the present invention provides a method for reducing biological contamination of indoor air, which method comprises:

providing a concentrated salt solution, which is either (i) a brine capable of responding to aeration thereof by a rapid increase of its Redox potential, wherein the rate of said increase is greater than the rate of increase observed for a 45% (w/w) calcium chloride solution subjected to identical aeration conditions; or (ii) a brine which is passed through an electrolytic cell in order to raise its Redox potential; Circulating said concentrated salt solution through a treatment zone; causing a stream of biologically contaminated air to flow through said treatment zone, such that said contaminated air is contacted with said salt solution in said treatment zone; and Withdrawing purified air from said treatment zone.

The term "brine" is used herein to indicate concentrated, nearly saturated or saturated salt solutions, namely, solutions wherein the concentration of the salt dissolved therein is preferably between 20%, and more preferably between 30% (w/w) and up to saturation at the relevant temperature.

The term "biologically contaminated air" is used herein to indicate that the air referred to contains clinically (or otherwise) undesired levels of bacteria, mycoplasma, protozoa, viruses (specifically Polio and Adeno viruses) and/or other types of microorganism. The term "purified air" is used herein to indicate that the level of microorganism in the air recovered by the method of the present invention has been reduced in a measurable quantity in comparison to the pre-treated air, preferably by at least 5%, and more preferably by at least 25% and most preferably by at least 50%.

The Redox potential of the concentrated salt solution is preferably not less than 200 mV, and more preferably not less than 300 mV, and most preferably not less than 400 mV during at least a portion of the time it is contacted with the biologically contaminated air. The Redox potentials reported herein are measured using Pt/Ag/AgCl arrangement, thus indicating the electrochemical potential which is developed between Pt electrode exposed to the brine and a standard silver-silver chloride electrode.

Two classes of concentrated salt solutions are suitable for use in the purification of the biologically contaminated air according to the present invention.

The first class of concentrated salt solutions includes brines which are capable of spontaneously developing high (e.g., above 300 mV) oxidation capacity in-situ, by simply contacting a stream of air to be purified with said brine, following which the brine is transformed into a powerful disinfectant, capable of considerably reducing the level of microorganisms in said stream of air. It should be noted that typical liquid desiccants, namely, a commercially available alkaline solution of lithium chloride (or lithium bromide), or a solution of calcium chloride, do not develop a sufficiently high Redox potential in response to a passage of air therethrough.

The second class of concentrated salt solutions to be used according to the present invention encompasses brines whose Redox potential is raised by passing the brine through an electrolytic cell.

More specifically, the first class comprises concentrated salt solutions which satisfy the following property: when the solution is subjected to aeration and the variation of its Redox potential is measured against time during said aeration period, then the rate of increase of said Redox potential is greater (preferably by more than 20%) than the corresponding rate measured, under identical aeration conditions, for a 45% (w/w) calcium chloride solution. The rate of variation of a Redox potential with time may be readily determined by plotting the same as a function of time, obtaining the derivative of said function and calculating its value for a certain point at time. However, for practical purposes, the variation of the Redox potential with time may be approximated by a suitable function, whose derivative represents the rate of variation of the Redox potential with time. Thus, most simply, the rate variation of the Redox potential of a solution is referred to herein as the difference between the Redox potential measured at two different points at time, which points are designated $t_1$ and $t_2$, divided by the difference in time $(t_2-t_1)$. Most conveniently, $t_1$ is taken as the starting point, before the solution is subjected to aeration (t=0), and $t_2$ may be chosen to be 60 minutes, 120 minutes, 180 minutes, 240 minutes or 300 minutes.

A simple set-up for determining the behavior of the Redox potential of a given salt solution in response to aeration thereof, and hence, its suitability for use in accordance with the present invention, is illustrated in FIG. 1. It should be noted that this set-up is provided as an example, and alternative arrangements may be used in order to collect the data required for plotting the Redox potential of given brine against time.

The set-up comprises an open vessel 100 having a volume of 12 liters, a spray head 101 (for example, in the form of a common shower head) positioned above said open vessel and connected thereto by means of a pipe 102. A pump 103 is used to circulate the solution in the device.

The solution is pumped from vessel 100 and returned thereto through spray head 101. The distance between the spray head 101 and the vessel is 20 cm and the number of openings in the spray head is 30 per 100 cm². The downwardly directed streams generated by spray head 101 are of course exposed to air, and hence the solution is aerated. The device further comprises a pair of electrodes 104 (namely, a working electrode made of platinum and a reference electrode (Ag/AgCl)) suitable for measuring a Redox potential of a solution contacted therewith, which electrodes are conveniently located upstream. Typically, the volume of the solution is in the range of 10 to 12 liters and it is allowed to circulate within the set-up described above at a rate of about 1 to 1.5 liter/min.

The initial Redox potential of a concentrated salt solution is typically in the range between 20 and 120 mV. The Redox potential of a salt solution circulated in the device varies (increases) in time, since the solution is contacted with air and is mixed therewith. During this aeration period, the Redox potential of the solution is measured at time intervals of about 15 to 30 minutes, and the results are plotted against time.

The set-up described in FIG. 1 was used to determine the variation with time of the Redox potential of two typical liquid desiccants, and the results are shown by means of bar diagrams in FIGS. 2a and 2b, for a 45% (w/w) calcium chloride solution and an alkaline 45% (w/w) lithium chloride solution, respectively. It may be seen that after an aeration period of about 120 minutes, the Redox potential of the calcium chloride solution reaches a value of about 180 mV. The average rate of increase of the Redox potential of the calcium chloride solution during this period of aeration is calculated as described above [(180 mV−50 mV)/120 min], and is approximately 1 mV/min. The average rate of increase of the Redox potential of the alkaline solution of the lithium chloride desiccant is calculated similarly (120 mV−20 mV)/120 min, and is about 0.8 mV/min for the first two hours of aeration of the liquid desiccant.

In contrast with the desiccants referred to above, the preferred concentrated salt solutions to be used according to the present invention are capable of developing a Redox potential of not less than 300 mV after having been circulated in the set-up described in FIG. 1 for 120 minutes. The average rate of increase of the Redox potential of the preferred solutions to be used according to the invention is therefore not less than 1.5 mV/min, and more preferably not less than 2.0 mV/min for the first two hours of aeration of the salt solution under the conditions of the set-up described in FIG. 1. Furthermore, under said conditions, the Redox potential of a salt solution suitable for use according to the invention exceeds 400 mV following an aeration period of 180 min.

Compositionally, the concentrated salt solution belonging to the first class identified above, which may be used according to the present invention for disinfecting the biologically contaminated air, is an aqueous solution containing one or more water soluble salts represented by the formulas MX, $M_2X$ and $MX_2$, wherein X is selected from the group consisting of chloride, bromide, iodide, sulfate and nitrate anions, and M indicates a metal cation, which is most preferably selected from the group consisting of sodium, potassium, calcium, magnesium and zinc, with the proviso than when X is chloride and M is other than zinc, then the solution comprises at least two water soluble salts. The presence of bromide and/or iodide anions in the concentrated salt solution is especially preferred.

A preferred concentrated salt solution, which may be used for disinfecting the biologically contaminated air, comprises zinc bromide or zinc chloride, or a mixture thereof, at a weight concentration of 40% to 55%. FIG. 3 is a bar diagram illustrating the variation with time of the Redox potential of 55% (w/w) zinc bromide and 55% (w/w) zinc chloride solutions. The data was collected using the set-up described in FIG. 1. It is apparent that the Redox potential of both zinc halide solutions increases rapidly with time. For Example, the average rate of increase of the Redox potential of the zinc bromide solution following two hours of aeration is greater than 3.0 mV/min.

Another preferred concentrated salt solution to be used according to the invention comprises a mixture of at least one bromide and/or iodide salt, and at least one chloride salt of one or more of the following metals: $Na^+$, $K^+$, $Mg^{2+}$ and $Ca^{2+}$. An especially preferred solution contains a mixture of bromide and chloride salts dissolved therein in a total concentration of 30 to 40% by weight, with the cationic species being $Mg^{2+}$, $Ca^{2+}$, $Na^+$ and $K^+$. More specifically, the concentrations of the aforementioned ions are as follows: $Mg^{2+}$: 30-50 g/liter; $Ca^{2+}$: 10-20 g/liter; $Na^+$: 30-50 g/liter; $K^+$: 5-10 g/liter; $Cl^-$: 150-240 g/liter; $Br^-$: 3-10 g/liter. An example of such a solution is provided by the Dead Sea brine, which has the following typical (average) mineral composition: $Mg^{2+}$: about 40.6 g/liter; $Ca^{2+}$: about 16.8 g/liter; $Na^+$: about 39.1 g/liter; $K^+$: about 7.26 g/liter; $Cl^-$: about 212.4 g/liter; $Br^-$: about 5.12 g/liter, with the total concentration of salts dissolved therein being 33% by weight.

A particularly preferred concentrated salt solution comprises a mixture of bromide and chloride salts dissolved therein in a total concentration of 30 to 40% by weight, with the cationic species being $Mg^{2+}$, $Ca^{2+}$, $Na^+$ and $K^+$, wherein the concentration of calcium chloride in said solution is effective in reducing the rate of evaporation of water therefrom, and is preferably in the range between 100 and 200 g/liter. When used in the purification process of the present invention, this especially preferred solution was found to develop a Redox potential of above 450 mV, combined with a very slow rate of evaporation of water therefrom.

FIG. 4 is a bar diagram which shows the variation with time of the Redox potential of a Dead Sea brine, having the composition described hereinabove, to which calcium chloride was added (in an amount of 150 g/liter). It may be seen that the solution comprising the Dead Sea brine and an additional amount of calcium chloride develops a Redox potential greater than 300 mV following two hours of aeration, and a Redox potential greater than 450 mV following four hours of aeration.

It has been observed that the Redox potential of the specific brines identified above, namely, the zinc halide brines and brines containing a mixture of at least one bromide salt and one chloride salt, such as the Dead Sea brine, is raised to above 300 mV after the brine has been circulated in the treatment zone in accordance with the present invention for a relatively short period of time (less than two hours), during which period it has been contacted and aerated with a stream of the biologically contaminated air. Thus, rather paradoxically, the medium to be purified according to the present invention, namely, a stream of biologically contaminated air, raises the Redox potential of the brine belonging to the first class (as defined above) which is mixed therewith, to such an extent that an in-situ aerated brine is generated, having strong disinfecting ability, such that said in-situ formed brine may be circulated within the treatment zone, continuously purifying the contaminated air flowing therethrough.

The second class of concentrated salt solutions to be used according to the present invention encompasses brines whose Redox potential is periodically raised by passing the brine through an electrolytic cell such that oxidants are generated in the brine, for example, chlorine, hypochlorite and hypochlorous acid, thus affording an oxidant brine, which is subsequently contacted with the air to be treated. Oxidant brines produced by means of electrolysis which may be used according to the present invention have a Redox potential of about 200-370 mV, and preferably 250-370 mV. The oxidant brine may be generated by passing a concentrated solution of one or more halide salts through an electrolytic cell. The term "halide salts", as used herein, specifically includes salts which contain a cation selected from the following group: $Li^+$, $Na^+$, $K^+$, $Mg^{2+}$ and $Ca^{2+}$. It has been surprisingly found that an oxidant brine of sodium chloride, having a concentration of 30 to about 40% by weight, functions as a powerful disinfectant under the conditions of the present invention.

It should be noted that the concentrated salt solution belonging to the first class identified above, namely, those solutions which spontaneously develop a high Redox potential (above 300 mV or even above 400 mV) in response to aeration thereof, may also be passed through electrolytic cell, if desired, in order to further intensify their oxidation capacity.

Accordingly, in a preferred embodiment, the present invention provides a method for treating a biologically contaminated air, which comprises causing a stream of biologically contaminated air to flow through a treatment zone, contacting said contaminated air with a concentrated salt solution circulating through said treatment zone and recovering a purified air therefrom, wherein the circulation of said solution comprises introducing the solution into the treatment zone, collecting the solution in a suitable vessel after it has been in contact with the contaminated air, driving the solution from said vessel and raising the Redox potential of the solution by passing said solution through an electrolytic cell, and reintroducing the solution into the treatment zone, in order to purify biologically contaminated air flowing therethrough.

The circulation of the concentrated salt solution, as describe above, may be conveniently carried out at ambient temperature; there is no necessity to heat the circulated salt solution.

The Redox potential of the brine is a readily measurable property, which may serve for monitoring the operation of the method provided by the invention. The measurement of the Redox potential is conveniently achieved by contacting the circulating brine, or a sample of the brine, with a suitable set-up, which set-up typically comprises a measuring electrode made of an inert metal or alloy (a platinum electrode) and a reference electrode (such as Ag/AgCl or calomel) connected to a voltmeter.

Depending on the results of the Redox potential measured by the set-up set forth above, or an alternative set-up, the Redox potential may be adjusted, e.g., by electrolyzing the brine, or enhancing the rate of air flow through the treatment zone, whereby the Redox potential is increased. Thus, the method provided by the present invention may further comprise periodically or continuously measuring the Redox potential of the brine solution, and adjusting the Redox potential of the brine based on the measured value of the Redox potential. Under routine mode of operation, the brine solution circulating within the treatment zone preferably has Redox potential in the range between 200 and 450 mV. Thus, if the measurement of the Redox potential indicates that the Redox potential is lower than 150 mV, then the electrolytic cell may be activated, in order to pass electrical current through the brine solution, whereby oxidant species are formed therein. As indicated above, certain brine solutions are capable of developing high Redox potential in response to enhanced aeration conditions. Accordingly, for these preferred brines as set forth above, the adjustment of the Redox potential may be accomplished by appropriately controlling the flow of air through the treatment zone.

The set-up which serves for measuring the Redox potential of the brine is positioned at any appropriate location in the pathway of the circulating brine, for example, inside the reservoir holding the brine, or in a conduit used to deliver the brine into the treatment zone. The measured Redox potential may then be used to provide one or more automatic feedback signals to the electrolytic cell or to the means serving for feeding the air into the treated zone, in order to adjust their operation. Alternatively or in addition, the electrolysis of the brine can be adjusted by a human operator based on the observed Redox potential. To this end, the measurement of the Redox potential may be used to generate an alarm signal, to trigger the interference of the human operator once the measurement of the Redox potential indicates a value outside a specified working range. Alternatively or in addition, an alarm signal may be generated once the measurement of the Redox potential indicates unacceptably low value (e.g., below 100 mV).

The term "electrolytic cell", as used herein, refers to a set-up comprising electrodes which are electrically connected to the opposite poles of a direct electrical current (DC) power supply. The electrolytic cell is placed in any suitable location in the pathway of the circulating brine. For example, two suitable electrodes are affixed within the reservoir used for storing the brine solution, or alternatively, within a conduit used to transfer the brine to the treatment zone. The electrodes are preferably placed in parallel to each other, separated by a gap of 0.3 to 2.0 cm, and more preferably of 0.5 to 1.0 cm. The electrodes are preferably in the form of plates or meshes having a length and a width of about 2 and 5 cm, respectively. The electrodes are generally composed of a material selected from the group consisting of titanium (coated with ruthenium oxide), platinum or an alloy of platinum and iridium. The cell typically operates at a current density of $10^3$-$10^5$ Ampere per square meter of anode, applying a voltage in the range between 2 and 10 V, and preferably about 3-5 V. Within the broad range of conditions described above, the electrolysis of a brine solution having a volume of about 10-100 liter may be carried out for about 5-10 minutes, with a current of few Amperes, following which the brine solution attains an operative Redox potential. It may be appreciated that the duration of the electrolysis may depend on the type and concentration of the brine used and the aeration conditions.

In the event that there is a need to decrease the Redox potential of the brine solution (for example, should the measured value exceeds 450 mV), then the brine is chemically treated with an effective amount of one or more oxidizer-scavenging compounds. The term 'oxidizer-scavenging compounds' is used herein to indicate organic and inorganic compounds which are useful in removing oxidizers (e.g., oxygen, halogens, oxyhalogens) from an aqueous solution. Oxidizer-scavenging compounds which act as reducing agents, and specifically, sulfur-based reducing agents, such as water soluble salts of sulfite, bisulfite, thiosulfate, metabisulfite, hydrosulfite or mixtures thereof, as well as other reducing agents such as ascorbic acid, are all within the scope of the present invention. The reducing agent may be fed into the oxidant brine in a solid or in a liquid form (e.g., as an aqueous solution). The measured Redox potential may then be used to provide one or more automatic feedback signals to a container which holds the solution of the reducing agent, in order to deliver suitable quantities of said reducing agent into the brine. For example, when the volume of the brine solution employed in the method of the present invention is between 10 and 100 liters, then about few milliliters of a solution of sodium bisulfite, or sodium thiosulfate, having a concentration of about 5% (w/v) may be used in order to decrease the Redox potential of the brine.

According to a particularly preferred embodiment, the method of the present invention comprises passing the stream of contaminated air through or onto one or more surfaces provided within the treatment zone, wherein said one or more surfaces are wetted by a concentrated salt solution circulating through said treatment zone, thereby increasing the liquid surface area in contact with the air, and recovering a purified air from said treatment zone. Most suitably, the treatment zone comprises one or more layers of absorbent material, small glass balls, ceramic rings or PVDF (poly vinilyden difluoride) rings, which are capable of providing high active surface area. According to one embodiment, the surfaces serving as the contact area for the air and the brine are in the form of layers made of absorbent fibrous material, which layers are wetted by one or more streams of a concentrated salt solution, wherein said streams flow in the treatment zone in an opposite direction to the flow of the contaminated air. The aforementioned arrangement of porous surfaces made of absorbent layers (e.g., cellulose fibers) that are mounted within the treatment zone, in combination with countercurrents of air and brine flowing therein, generates an increased liquid surface area in direct contact with the air to be treated, allowing the brine to carry out its disinfection action effectively.

In another aspect, the present invention provides an apparatus suitable for reducing the biological contamination of indoor air, which comprises:

- a chamber having at least first and second openings for receiving a stream of biologically contaminated air and for withdrawing purified air therefrom;
- means for causing a stream of air to flow into said chamber and outwardly therefrom through said first and second openings, respectively;
- a basin located beneath said first opening;
- a pump and one or more conduits connecting said basin to the interior of said chamber, wherein said pump and conduit(s) are suitable for withdrawing a brine from said basin and feeding the same into the interior of said chamber;
- a first pair of electrodes positioned in said one or more conduit(s), wherein said electrodes are electrically connected to the opposite poles of a direct electrical current (DC) power supply; and
- a second pair of electrodes positioned in said one or more conduit(s), capable of measuring the Redox potential of a brine passing therethrough.

Means for causing a stream of air to flow into the chamber and outwardly therefrom may be a fun, a suction pump or a centrifuge compressor air supply. Most preferably, one or more surfaces capable of increasing the contact area between air and liquid are mounted within the chamber. For example, the chamber is preferably provided with a fill having high active surface area, typical to fibrous materials or small glass balls or ceramic rings, or PVDF (poly vinilyden difluoride) rings. According to a specific embodiment, the chamber has a fill assembly positioned therein, which assembly is in the form of a three-dimensional matrix composed of a plurality of grids spaced from one another and disposed in perpendicular planes to form essentially cubic spaces therebetween, into which spaces absorbent fibrous material may be introduced. The grids may be made of polypropylene and have a thickness of about 0.5 mm to 1 mm. The side of the cubic space that is filled with the fibrous material, as mentioned above, may vary in the range of 3 to 5 cm. In operation, the air to be purified and the brine are brought into intimate contact within the surfaces made by said fibrous absorbent material, which surfaces are being supported by means of said fill assembly within the chamber.

FIG. 5 schematically illustrates an apparatus 10 for effectively reducing microbiological load in air according to a preferred embodiment of the invention. Apparatus 10 comprises an elongated, vertically positioned treatment zone 17 (for example, an open counterflow tower) having a first opening 32 and a second opening 33 in the lowermost and uppermost sections thereof, for receiving an upward stream of biologically contaminated air 15, and for withdrawing a purified air 14 from said tower, respectively. A fan 11 (or a suction pump) fitted at the upper opening 33 is adapted to generate a negative pressure inside the tower 17, thus producing air suction, causing a stream of biologically contaminated air (designated by arrows 15) to flow upwardly in tower 17 and outwardly therefrom. The fan 11 generally provides air suction rates of about 2000 cubic meters/hr.

The tower 17 further comprises a plurality of sprinkles or spray heads 23 mounted in an upper section thereof. The brine is drawn from a basin 22 positioned below opening 32 by means of a fluid pump 21, and is delivered into the interior of tower 17 by means of a suitable ductwork 28 and the aforementioned sprinkles or spray heads 23 connected thereto. Streams of brine 24, generated by said sprinklers, flow downwardly inside tower 17 and are collected in basin 22, thus allowing the circulation of the brine.

The dimensions and shape of tower 17 may be readily selected by the skilled artisan. In general, the cross section area of tower 17 is in the shape of a square or a circle. The walls of tower 17 may be made of various materials such as plastic, polyethylene, polypropylene, polyester, fiberglass or suitable stainless steel (AISI 304, 316, 410, 420 and 430). In general, it has been found that a brine solution circulating at a rate of 3 to 15 $m^3$/hr is capable of effectively purifying a stream of air drawn by the fun at a rate of 400 to 2000 $m^3$/hr.

The interior of tower 17 serves to contact the brine 24 sprinkled at the upper section of said tower with the stream of the biologically contaminated 15 driven upwardly in the tower and outwardly therefrom, by fan 11. In this way, the microorganisms contaminating the air are exposed to the saline and undergo proteins and DNA denaturation which disables their ability to reproduce and thus shorten their life span. As will be discussed hereinbelow, this operation when continuously carried out in closed spaces (e.g., buildings), substantially reduces the amount of indoor airborne microbiological contamination therein.

Tower 17 preferably comprises one or more absorbent layers (designated 18*a*, 18*b*, . . . , 18*n*) disposed therein, such that the upwardly directed air stream 15 is forced to pass through said layers. Absorbent layers 18 may be positioned essentially perpendicularly to the longitudinal axis of tower 17, as illustrated in the figure. These layers may be affixed to the internal walls of the tower by conventional means (not shown). Alternatively, a fill assembly that is conventionally used in cooling towers may be placed in tower 17, and the spaces of said fill assembly may be loaded with the absorbent material. Absorbent layers 18 are wetted by the downwardly flowing streams 24 of the brine and become impregnated therewith, thus allowing improved contact between the contaminated upwardly directed air stream 15 passing therethrough and the brine 24. Absorbent layers 18 are generally made of cellulose fibers and have a thickness in the range of 3 to 7 cm, preferably about 5 cm. It has been found that the preferred number of absorbent layers provided within tower 17 is 3 to 5. It should be noted that in order to increase the contact surface area between the liquid and the air to be treated, tower 17 may be provided with means conventionally employed for such purposes, for example, Rasching rings, made of ceramic material or plastic material such as PVDF (poly vinylidene difluoride) or PP (polypropylene) or PE (polyethylene) that are commonly used in distillation columns.

Apparatus 10 further includes an electrolytic cell (EC), 30 for generating an oxidant brine having a desired Redox potential. In its most simple configuration, an electrolytic cell suitable for use according to the present invention comprises two electrodes that are affixed within conduit 28 and placed in parallel to each other, separated by a distance of 0.3 to 2.0 cm, and more preferably of 0.5 to 1.0 cm. The electrodes are preferably in the form of plates or meshes having a length and a width of about 2 and 5 cm, respectively. The electrodes are generally composed of a material selected from the group consisting of titanium (possibly coated with ruthenium oxide), platinum or an alloy of platinum and iridium. The electrodes are electrically connected to the opposite poles of a direct electrical current (DC) power supply.

In operation, the brine pumped from basin 22 passes in the electrolytic cell 30, which operates under 2 to 3.5 V, at a rate of about 3 to 15 $m^3$/hour, whereby the brine is electrolyzed. Upstream there is provided a Redox potential measurement device (RDX) 31, for determining the Redox potential of the oxidant brine. Such a device includes a working electrode made of platinum, exposed to the stream of the optionally electrolyzed brine, and a conventional reference electrode (Ag/AgCl). The brine having a Redox potential in the range of 200 to 500 mV, and more preferably 300 to 450 mV, flows into tower 17 and is contacted therein with an upwardly directed stream of biologically contaminated air 15. The brine then exits tower 17 by force of gravity through opening 32 and is being collected in basin 22, from which it is recycled in the apparatus.

In one specific preferred embodiment of the invention apparatus 10 further comprises a control unit 35 electrically connected (designated by dotted arrowed lines) to fan 11, pump 21, electrolytic cell 30, and RedOx potential measurement device 31. Control unit 35 is adapted for monitoring and managing the operation of apparatus 10 responsive to signals received from RedOx potential measurement device 31, in particular, the operation of electrolytic cell 30 employed for electrolyzing the brine solution passing in ductwork 28 during operation, and the operation of fan or suction pump 11 for adjusting the rate of contaminated air 15 flowing into apparatus 10.

Optionally, apparatus 10 further comprises key pad 35*k* and display unit 35*d* (e.g., dot matrix or LCD) electrically connected to control unit 35, for receiving inputs from an operator, and for providing the operator output indications regarding the operation of apparatus 10. Of course, apparatus 10 may comprise additional means connected to control unit 35 for generating output indications (e.g., leds, speakers).

Control unit 35 may be implemented by a specially designed control logic circuitry, preferably by a programmable microcontroller. At least one analog to digital converter may be needed by control unit 35 for converting the signals received from RedOx measurement device 31.

Apparatus 10 preferably further comprises a container 36, for holding a solution of oxidizer-scavenging compounds 36*c*, wherein said container communicates with basin 22 through pipe 36*p*. The passage through pipe 36*p* may be controlled by means of valve 36*v*, electrically connected to control unit 35, for controlling the feeding of the solution of the oxidizer-scavenging compounds into the brine 2 in order to reduce its Redox potential.

Control unit 35 is preferably adapted for activating apparatus 10 responsive to inputs received from key pad 35*k* (or an on/off switch—not shown), by issuing respective control signals for activating pump 21 for pumping brine 2, and fan 11 for introducing contaminated air 15 stream in rates suitable for normal operation of apparatus 10 e.g., 1000 to 1500 $m^3$/hr. Control unit 35 is preferably adapted to adjust the performance of apparatus 10 responsive to readings received from RedOx measurement device 31. In particular, the RedOx potential of brine 2 may be adjusted by varying the rate of flow of contaminated air 15 introduced into apparatus 10, such that control unit 35 may be adapted to increase the rotation speed of fan 11, for increasing the rate of contaminated air stream e.g., 1500 to 2000 m$^3$/hr introduced into apparatus 10, responsive to low RedOx potential readings e.g., less than 150 millivolts.

Additionally or alternatively, control unit 35 may be further adapted to activate the electrolytic cell 30 responsive to low RedOx readings e.g., less than 150 millivolts. On the other hand, if the measurement of the potential indicates unacceptably high RedOx potential in brine 2, then control unit may issue control signals for opening valve 36v for introducing a small quantity (e.g., drops) of the oxidizer-scavenging compounds 36c contained in container 36, whereby the brine solution attains a normal Redox potential e.g., 200-400 millivolts.

It should be noted that the method and apparatus provided by the present invention may be effectively used for purifying air in many different kinds of large closed spaces. In addition to hospitals, which were already indicated hereinabove, poultry farms, greenhouses, tunnels, train stations and spaces exposed to heavy smoking may also be specifically mentioned. The method and apparatus of the invention are useful as a prophylactic measure for preventing avian flu, sick buildings syndrome (SBS) and other viral diseases. Specifically, it has been found that Dead Sea brine having the composition described above is useful in significantly reducing the level of the following microorganisms in the treated air:
Bacteria—*E. coli, K. pneumonia, S. aureus, P. aeruginosa* and *Bacillus* species.
Fungi—*Aspergillus* species.
Viruses—Polio Virus and Adeno Virus.

BRIEF DESCRIPTION OF THE DRAWINGS

FIG. 14 is a bar diagram showing the results obtained upon running the apparatus of the invention using a Dead Sea brine.

FIG. 15 is a bar diagram which illustrates the air quality in a hospital department treated according to the invention, and a non-treated department.

EXAMPLES

Figure 1:
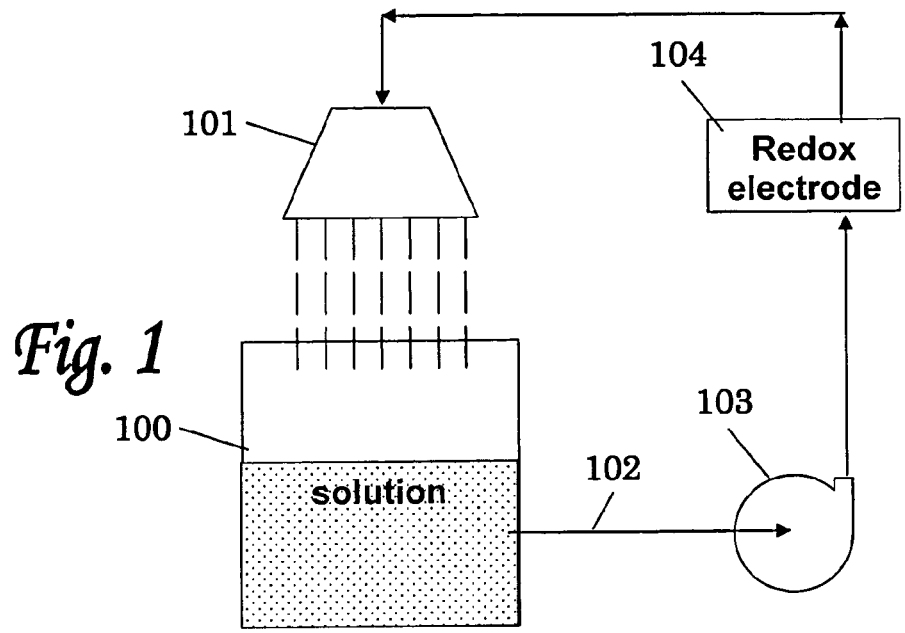
FIG. 1 schematically illustrates an arrangement suitable for measuring the Redox potential of a brine subjected to aeration.
Figure 2A:
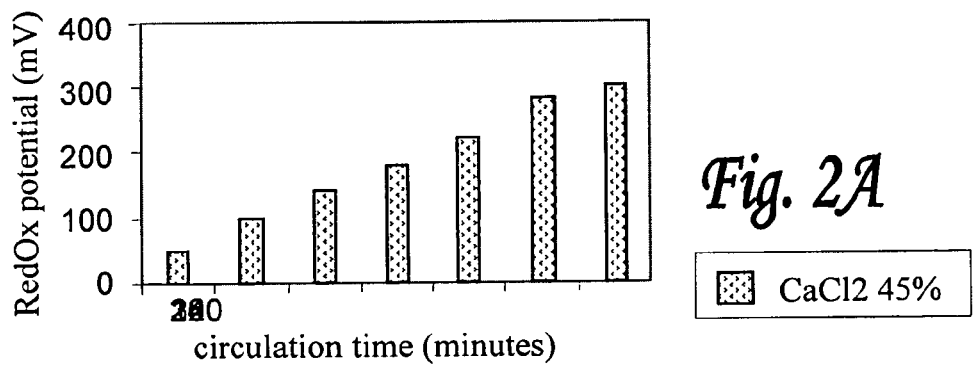
FIGS. 2a and 2b are bar diagrams showing the Redox potential of calcium chloride and alkaline lithium chloride solutions as a function of time.
Figure 2B:
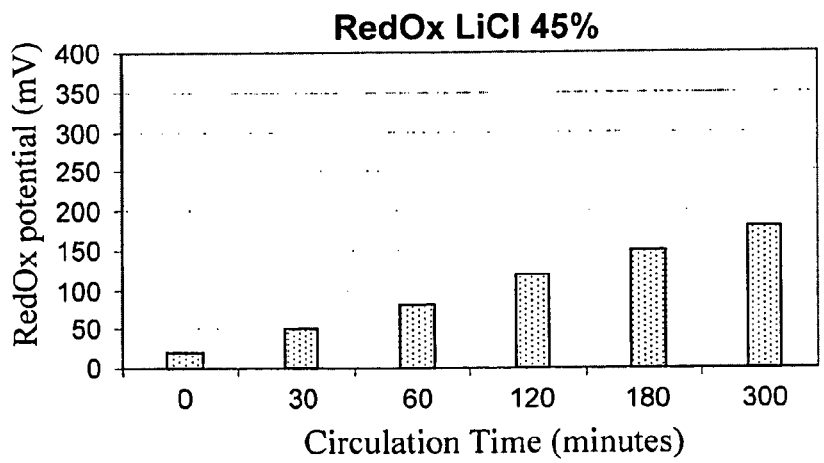
Figure 3:
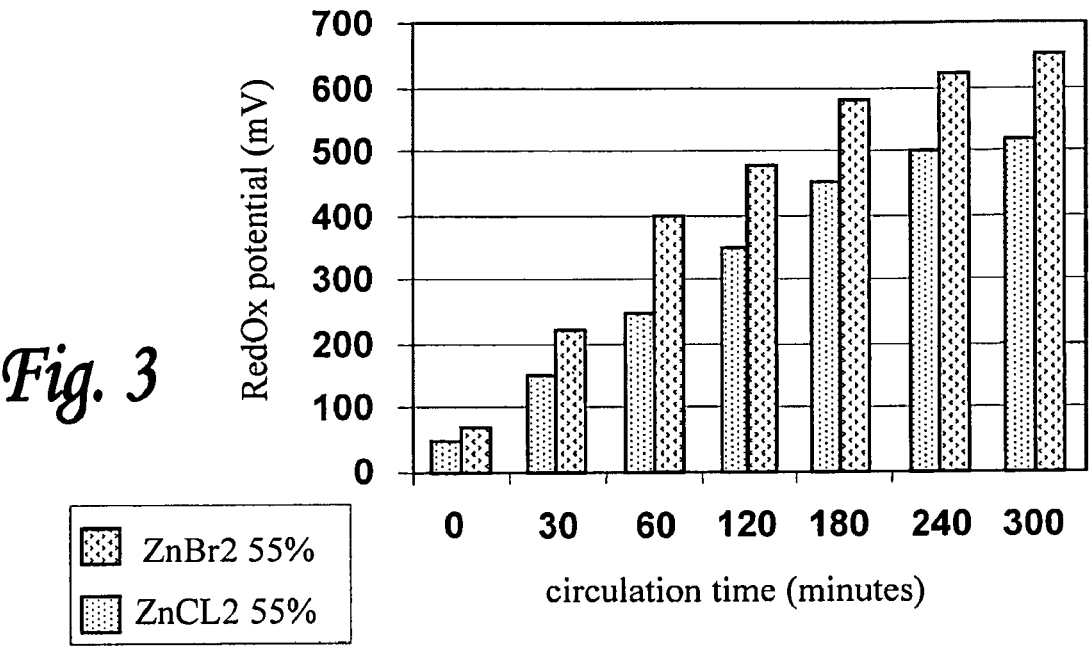
FIG. 3 is a bar diagram showing the Redox potential of zinc halide solutions as a function of time.
Figure 4:
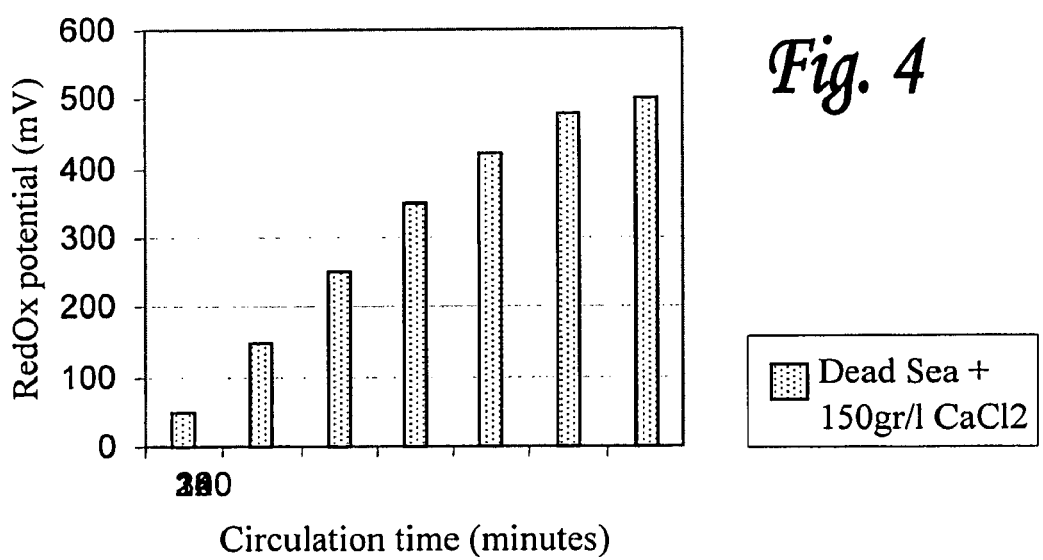
FIG. 4 is a bar diagram showing the Redox potential of a Dead Sea brine as a function of time.
Figure 5:
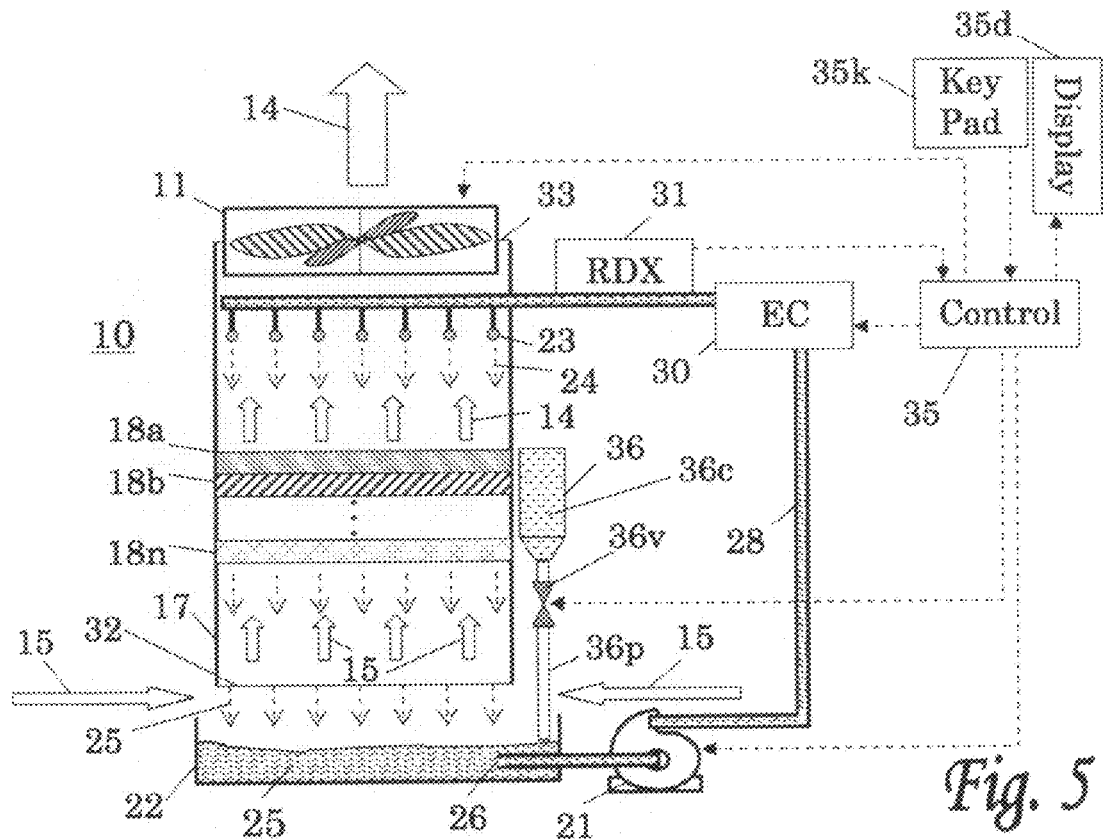
FIG. 5 schematically illustrates an apparatus for effectively reducing the amount of microbiological organisms residing in air.

Examples 1 to 5 describe the results of tests which were carried out with the apparatus illustrated in FIG. 5 in the 5$^{th}$ floor of the bone-marrow department of the Chaim Sheba Medical Center in Tel-Hashomer, Israel. The apparatus was placed in a corridor (equipped with no air-conditioning means), and was operated over a month under various conditions, as discussed below. During the tests the corridor was is air connection with the stairway and elevator system of the medical center. The volume of the corridor space was approximately 700 m$^3$.

The height of the apparatus was 200 cm, and the dimensions of its cross-section area were 50 cm×50 cm. The apparatus operated under the following conditions:
The rate of air suction during the tests was 400 m$^3$/H.
The brine used was an aqueous solution of sodium chloride having 35% salinity or a Dead Sea Brine. The brine was pumped at a rate of 10 m$^3$/hour.

The electrolytic cell included two titanium electrodes coated with an alloy of ruthenium oxide, commercially available from Denura LTD, Italy. These electrodes were placed in parallel within the conduit connecting the basin and the top of the tower. The gap between the electrodes was of 1 cm.

The electrodes used to measure the Redox potential of the brine were a platinum electrode and silver/silver chloride electrode, commercially available from Trytel IL.

The absorbent layers used are made of natural cellulose fibers. Each layer consisted of 4 cm thick fibrous material, placed in the lower section of the tower, in the vicinity of the first (lowermost) opening thereof.

Air samples of the air entering (hereinafter incoming airflow) and leaving (hereinafter outgoing airflow) the apparatus were collected by an air sampler onto general microbial colonies TSA+5% SB (Tryptone Soya Agar+5% Sheep Blood) settle plates and onto yeast and fungal colonies SDA (Sabouraud Dextrose Agar) settle plates. The TSA+5% SB plates were incubated at 37° C. for 24 to 48 hours, the SDA plates were incubated at 37° C. for 24 to 48 hours, and the results are reported in Colony Forming Units (CFUs) per cubic meter.

Example 1

Comparative

Figure 6:
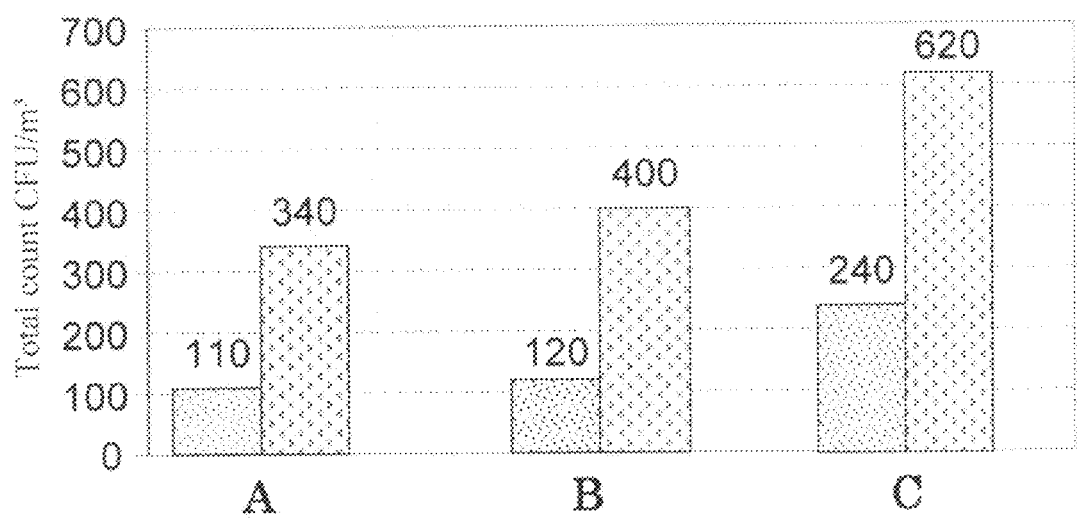
FIG. 6 is bar diagram showing the reduction of microbial load in air following treatment with a non-electrolyzed brine.

The Efficacy of a Non-Electrolyzed Brine as a Disinfectant for Biologically Contaminated Air The apparatus illustrated in FIG. 5, containing two absorbent layers mounted therein, was operated without activating the electrolytic cell, as follows:
NaCl brine is pumped from the basin and is circulated through the apparatus. After 0.5 hour, the Redox potential of the circulating brine is periodically measured at intervals of 20 minutes and air samples (of the incoming contaminated airflow and the outgoing purified airflow) are concurrently collected onto a TSA+5% SB settle plates. The bar diagram shown in FIG. 6 and the table below summarize the results obtained. In the accompanying bar diagrams, a pair of adjacent columns represents the level of microbial contamination (CFU/m$^3$ units) measured in the incoming, contaminated airflow (right column) and the outgoing, purified airflow (left column). A pair of adjacent columns is designated by a capital letter or by the time at which the measurement was taken.

| Measurement | Redox potential (mV) | Microbial contamination incoming air flow (CFU) | Microbial contamination outgoing air flow (CFU/m$^3$) |
| --- | --- | --- | --- |
| 1 | 140 | 340 | 110 |
| 2 | 180 | 400 | 120 |
| 3 | 185 | 620 | 240 |

Example 2

The Effect of the Number of Absorbent Layers Provided within the Tower on the Efficacy of the Air Purification The apparatus illustrated in FIG. 5, containing either one, two or three layers of absorbent material horizontally deposited therein, is operated as follows:

NaCl brine is pumped from the basin and passed through the electrolytic cell (3 V) to produce an oxidant brine having a Redox potential of about 200 to 250 mV. The oxidant brine is circulated through the apparatus for about 1 to 2 hours, during which period air samples (of the incoming contaminated airflow and the outgoing purified airflow) are periodically collected onto a TSA+5% SB settle plates.

Figure 7:
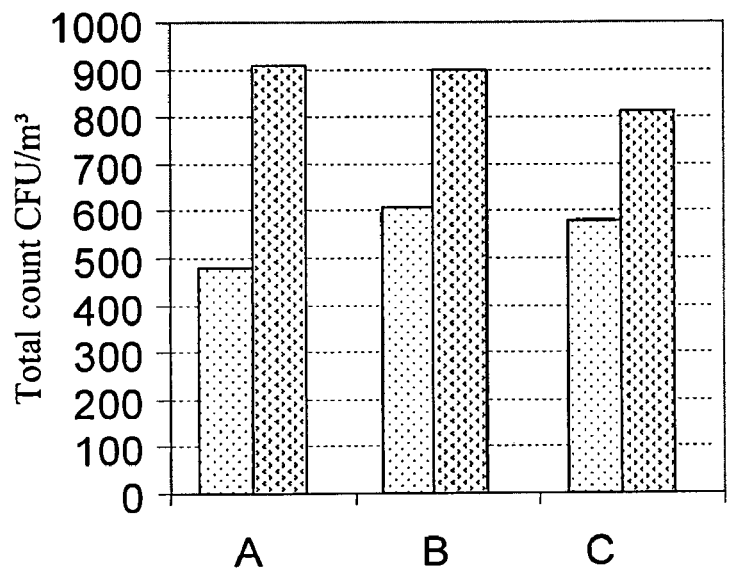
FIG. 7 is a bar graph showing the reduction of microbial load upon operating the apparatus of the invention with a single absorbent layer.
Figure 8:
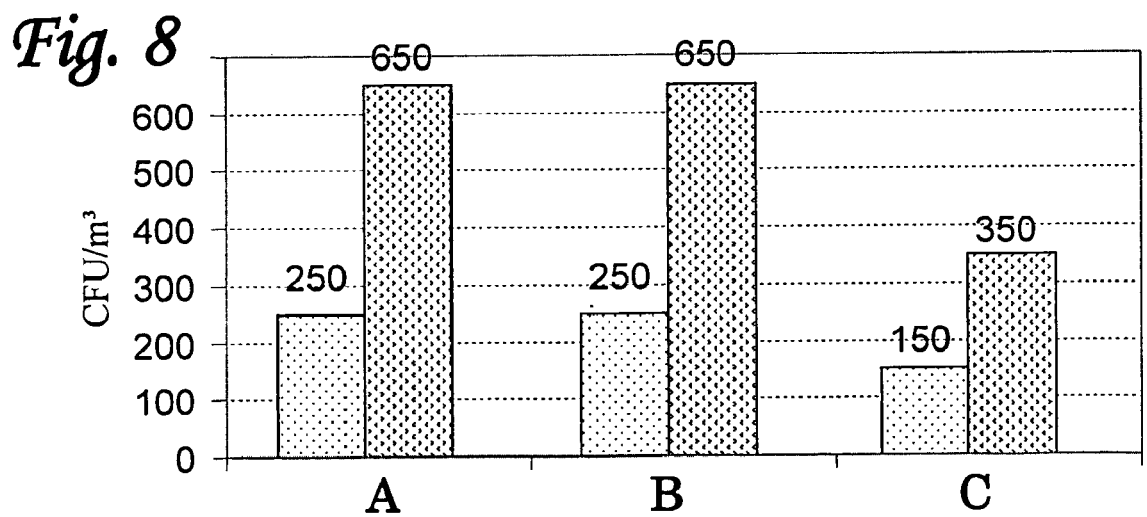
FIG. 8 is a bar diagram showing the reduction of microbial load upon operating the apparatus of the invention with two absorbent layers.
Figure 9:
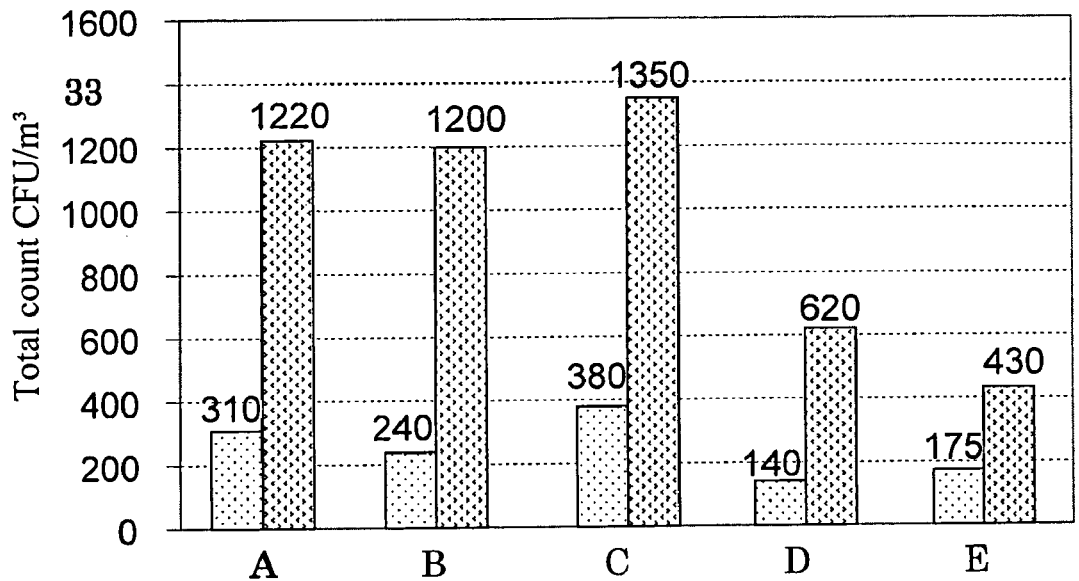
FIG. 9 is a bar diagram showing the reduction of microbial load upon operating the apparatus of the invention with three absorbent layers.

The bar diagrams shown in FIGS. 7, 8 and 9 summarize the results obtained for the use of one, two and three absorbent layers in the tower, respectively. These results are also indicated in the table below:

TABLE 2

| Number of absorbent layers | Microbial contamination incoming air flow (CFU/m$^3$) | Microbial contamination outgoing air flow (CFU/m$^3$) |
| --- | --- | --- |
| 1 | 910 | 480 |
| 1 | 900 | 610 |
| 1 | 810 | 580 |
| 2 | 650 | 250 |
| 2 | 650 | 250 |
| 2 | 350 | 150 |
| 3 | 1220 | 310 |
| 3 | 1200 | 240 |
| 3 | 1350 | 380 |
| 3 | 620 | 140 |
| 3 | 430 | 175 |

Example 3

Figure 10:
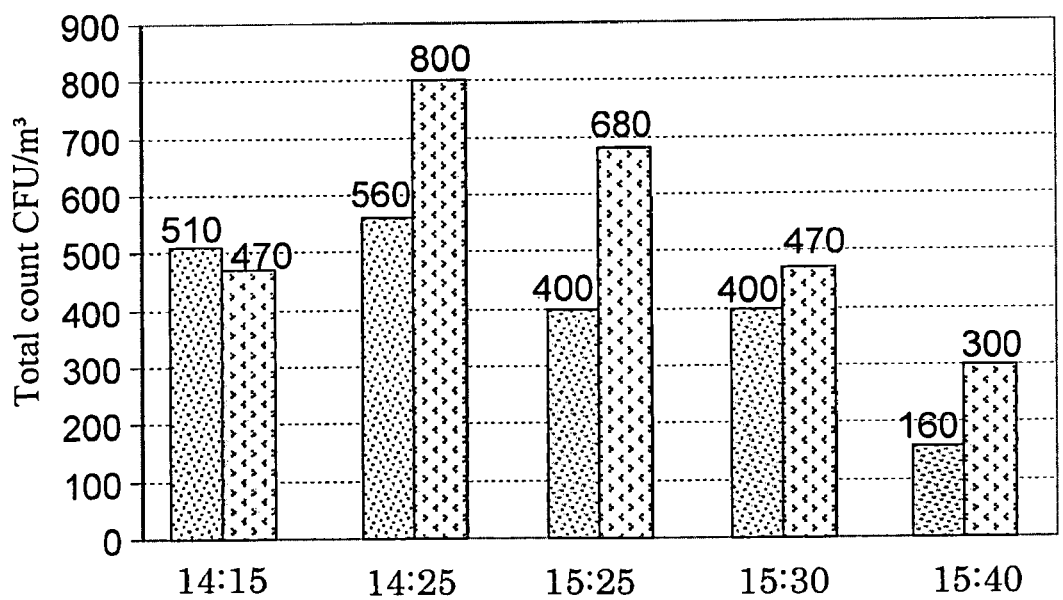
FIG. 10 is a bar diagram showing the results obtained upon running the apparatus continuously.

The apparatus was allowed to operate continuously, with 3 layers of cellulose fibers provided therein. The Redox potential of the circulating brine was about 230 mV. Air samples were collected periodically from both the incoming airflow and the outgoing airflow. FIG. 10 is a bar diagram showing the Colony Forming Units (CFUs) per cubic meter determined for a sample taken from the incoming air and the outgoing air (right and left columns, respectively) at different times (starting at 14:15 PM). A decay in the microbial load is observed over time.

Example 4

Figure 11A:
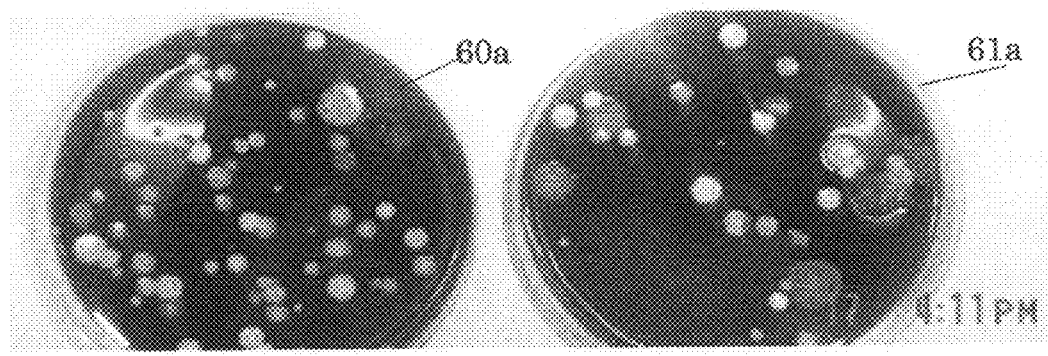
FIGS. 11A to 11C are photos showing microbiological growth in TSA+5% SB settle plates of samples taken from the incoming and outgoing airflows of the apparatus of the invention operating with a single absorbent layer.
Figure 11B:
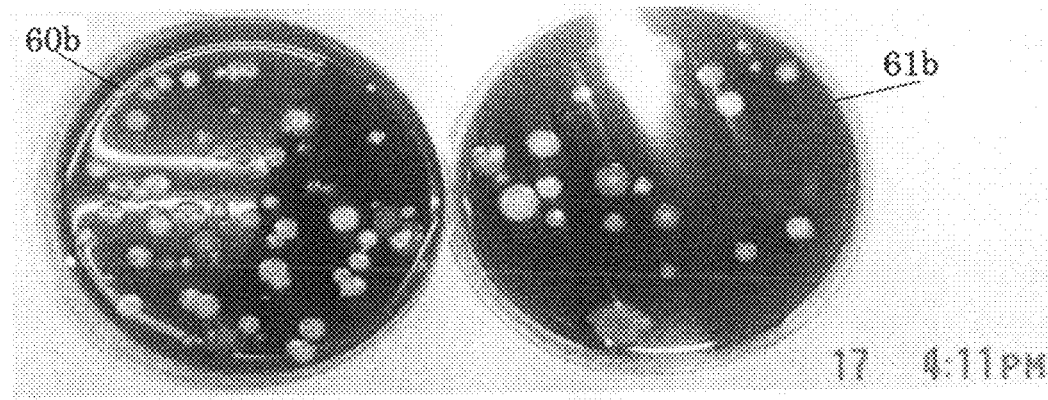
Figure 11C:
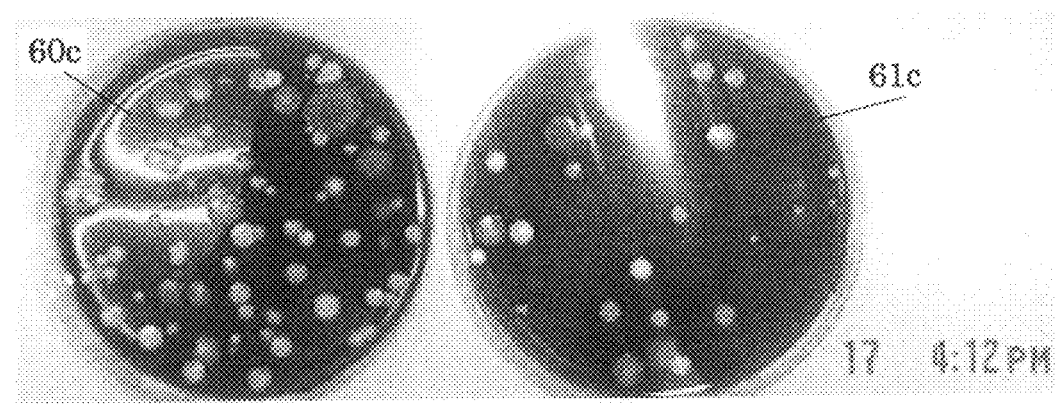

The apparatus shown in FIG. 5 was operated using a single layer of absorbent material mounted therein. The electrolytic cell was activated to generate an oxidant brine having a Redox potential of about 250 mV circulating through the apparatus, and air samples were taken periodically (at 12:00 PM, 12:40 PM and 12:50 PM) from both the incoming airflow and the outgoing airflow. FIGS. 11a, 11b and 11c are photos of the TSA+5% SB settle plates, wherein the Petri dishes seen in the left (designated 60a, 60b and 60c) show the development of microbial colonies originating from samples taken from the incoming, contaminated air, while the Petri dish in the right (61a, 61b and 61c) show the development of microbial colonies originating from samples taken from the treated, purified air. It is apparent from the photos that the purification treatment according to the invention effectively reduces the amount of microbial contamination in air.

Figure 12A:
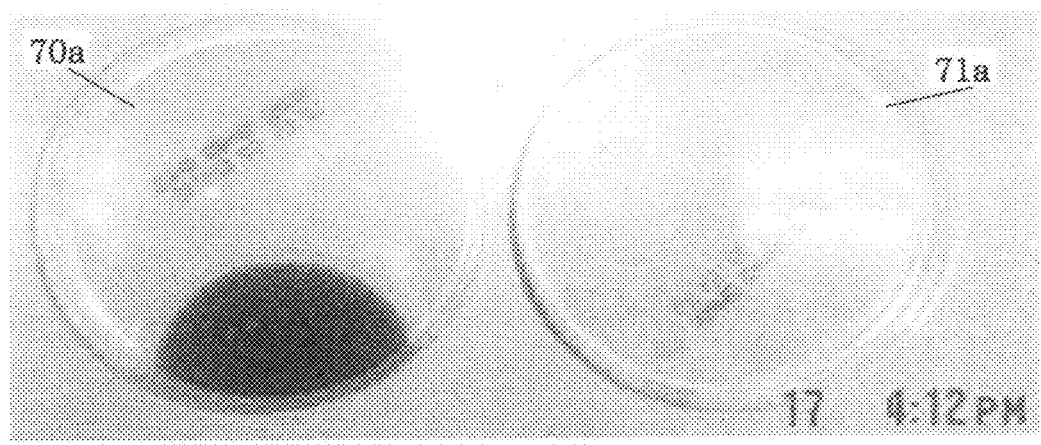
FIGS. 12A and 12B are photos showing the development of yeast in SDA settle plates containing samples taken from the incoming and outgoing airflows of the apparatus of the invention operating with a single absorbent layer.
Figure 12B:
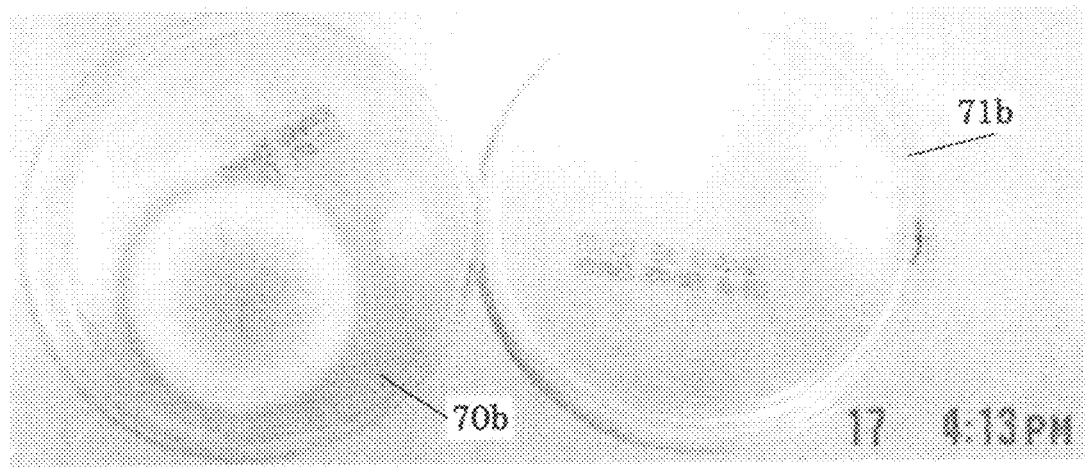
Figure 13A:
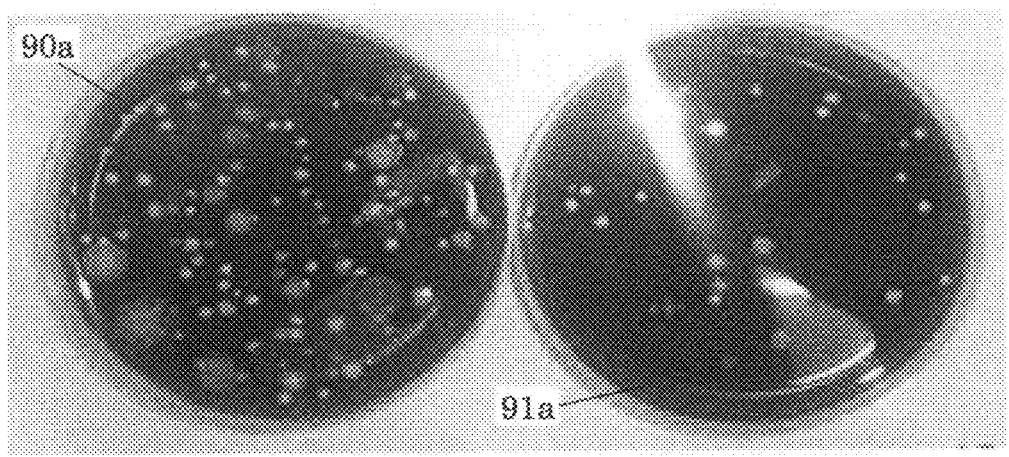
FIGS. 13A to 13E are photos showing microbiological growth in TSA+5% SB settle plates of samples taken from the incoming and outgoing airflows of the apparatus of the invention operating with two absorbent layers.
Figure 13B:
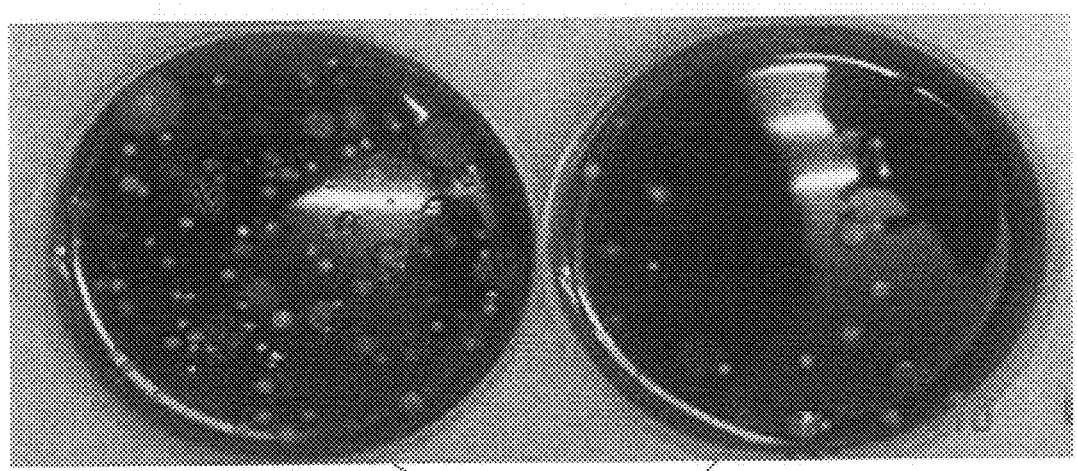
Figure 13C:
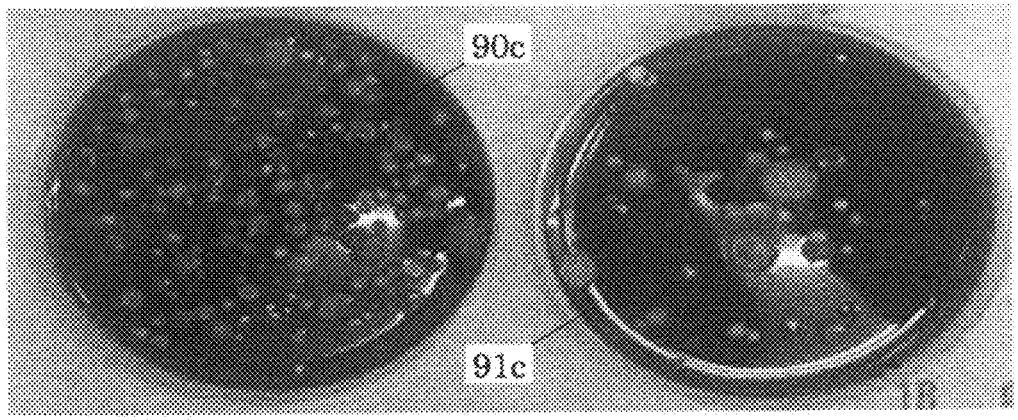
Figure 13D:
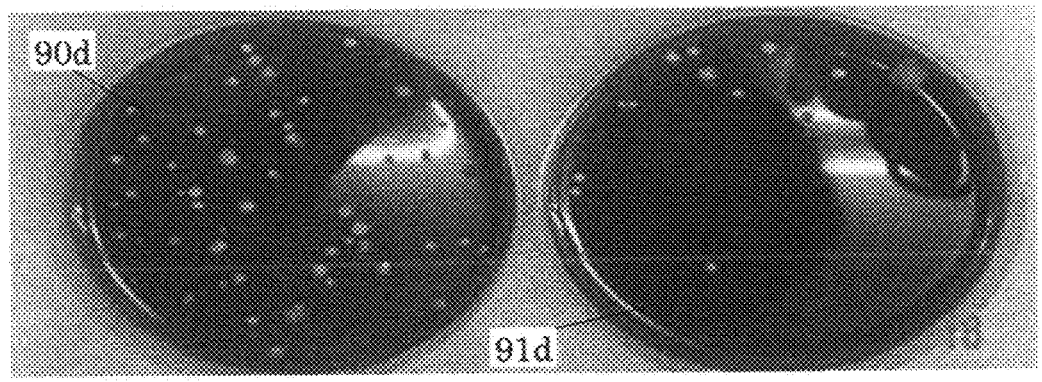
Figure 13E:
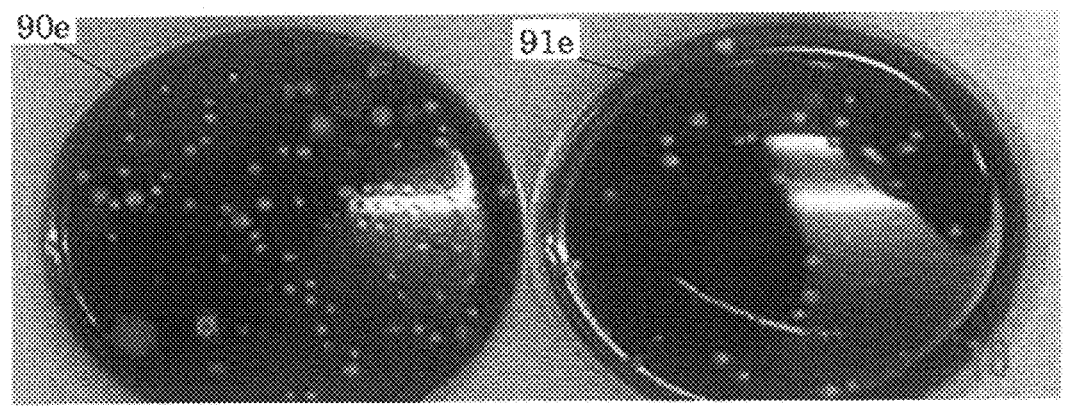

A similar observation may be readily made on the basis of the SDA settle plates shown in FIGS. 12a and 12b. No bacterial colonies are visible in the Petri dishes designated 71a and 71b, where samples taken from the outgoing, treated air were seeded. In contrast, visible colonies have developed in the Petri dishes designated 70a and 70b, where samples taken from the incoming, pre-treated air were seeded.

Example 5

A similar experiment to that described in Example 4 was carried out, but this time the apparatus was operated with two layers of cellulose fibers mounted therein. The Redox potential of the circulating brine was about 230-250 mV. Air samples were taken periodically from both the incoming airflow and the outgoing airflow. It is apparent from FIGS. 13a to 13E that the development of microbial colonies originating from samples taken from the outgoing, treated airflow (the Petri dishes designated 91a-91e) is considerably reduced in comparison to the corresponding samples, taken from the incoming, non-treated airflow (the Petri dishes designated 90a-90e).

Example 6

The Efficacy of a Non-Electrolyzed Brine which Comprises a Mixture of Halide Salts as a Disinfectant for Biologically Contaminated Air This example describes the results of tests that were carried out with the apparatus illustrated in FIG. 5 in the intensive care children department of the Chaim Sheba Medical Center in Tel-Hashomer, Israel. The apparatus was connected to the air-conditioning system of the department. The volume of the department space was approximately 1000 m$^3$; the rate of air suction of the air-conditioning system during the tests was about 2000 m$^3$/hour while the rate of air suction through the apparatus of the invention was about 700 m$^3$/hour. Fresh air from outside was fed into the apparatus, in a volumetric concentration of 15% relative to the total volume of air circulated.

The brine used was a Dead Sea brine, whose composition was identified above, which brine further includes $CaCl_2$ in a concentration of 200 g/lit. The brine was pumped at a rate of 10 m$^3$/hour.

FIG. 14 is a bar diagram which describes the level of biological contamination measured in the children's intensive care department at the Sheba hospital (Israel) over a period of approximately two weeks. In the first week (the control week—between September 13 and September 20) high levels of contamination were measured. In the subsequent week the apparatus according to the invention was allowed to operate as described above, and a significant reduction in the biological contamination in the air of said department was observed.

For the purpose of comparison, the quality of the air was also tested in an adjacent department—the interim care department (which was not treated by means of the method of the invention). The measurements were carried out twice a day both in the treated and untreated departments over a period of approximately two weeks, and the results collected are shown in FIG. 15, which is a bar diagram describing the level of contamination (CFU/m$^3$) against time. It may be seen that the level of contamination in the treated department was consistently lower in comparison to the untreated department.

It is thus apparent from FIGS. 14 and 15 that a concentrated salt solution which comprises a mixture of halide salts forms a particularly powerful disinfectant.

The invention claimed is:

1. A method for reducing biological contamination of indoor air, which method comprises:
   providing a concentrated salt solution, which is either (i) a brine capable of responding to aeration thereof by a rapid increase of its Redox potential, wherein the rate of said increase is greater than the rate of increase observed for a 45% (w/w) calcium chloride solution subjected to identical aeration conditions; or (ii) a brine which is passed through an electrolytic cell in order to raise its Redox potential, wherein chlorine, hypochlorite and hypochlorous acid are generated in said brine;
   circulating said concentrated salt solution through a treatment zone; causing a stream of biologically contaminated air to flow through said treatment zone, such that said contaminated air is contacted with said salt solution in said treatment zone; wherein the Redox potential of the concentrated salt solution in the treatment zone is from 200 mV to 370 mV; and withdrawing purified air from said treatment zone.

2. A method according to claim 1, wherein the concentrated salt solution is a brine capable of responding to aeration thereof by a rapid increase of its Redox potential, wherein the rate of said increase is greater than the rate of increase observed for a 45% (w/w) calcium chloride solution subjected to identical aeration conditions.

3. A method according to claim 2, wherein the brine contains one or more water soluble salts represented by the formulas MX, M$_2$X and MX$_2$, wherein X is selected from the group consisting of chloride, bromide, iodide, sulfate and nitrate anions, and M indicates a metal selected from the group consisting of sodium, potassium, calcium, magnesium and zinc, with the proviso than when X is chloride and M is other than zinc, then the solution comprises at least two water soluble salts.

4. A method according to claim 2, wherein the brine comprises a bromide salt and/or an iodide salt.

5. A method according to claim 3, wherein the brine comprises zinc bromide, zinc chloride, or calcium bromide or a mixture thereof.

6. A method according to claim 3, wherein the brine comprises a mixture of at least one bromide salt and at least one chloride salt of one or more of the following cations: Na$^+$, K$^+$, Mg$^{2+}$ and Ca$^{2+}$.

7. A method according to claim 6, wherein the total concentration of salts dissolved in the brine is in the range between 30 and 40% by weight.

8. A method according to claim 7, wherein the brine comprises calcium chloride in a concentration effective of reducing the evaporation of water therefrom.

9. A method according to claim 1, wherein the concentrated salt solution is a brine solution which is passed through an electrolytic cell in order to raise its Redox potential.

10. A method according to claim 9, wherein the brine comprises sodium chloride in a concentration of between 30 and 40% by weight.

11. A method according to claim 1, comprising passing the stream of contaminated air through or onto one or more surfaces provided within the treatment zone, wherein said one or more surfaces are wetted by the concentrated salt solution circulating through said treatment zone, thereby increasing the liquid surface area in contact with the air.

12. A method according to claim 11, wherein the surfaces provided within the treatment zone comprise one or more layers of absorbent material, small glass balls, ceramic rings and plastic rings.

13. A method according to claim 12, wherein the surfaces are in the form of layers made of absorbent fibrous material, which layers are wetted by one or more streams of the circulating salt solution, which streams flow in the treatment zone in a direction which is opposite to the flow of the contaminated air.

14. A method for treating a biologically contaminated air according to claim 1, which comprises causing a stream of biologically contaminated air to flow through a treatment zone, contacting said contaminated air with a concentrated salt solution circulating through said treatment zone and recovering a purified air therefrom, wherein the circulation of said solution comprises introducing the solution into the treatment zone, collecting the solution in a suitable vessel after it has been in contact with the contaminated air, driving the solution from said vessel and raising the Redox potential of the solution by passing said solution through an electrolytic cell, and reintroducing the solution into the treatment zone, in order to purify biologically contaminated air flowing therethrough.

15. A method according to claim 14, wherein the concentrated salt solution is circulated at ambient temperature.

16. A method according to claim 1, wherein the indoor air which is purified is the indoor air of a hospital, a poultry farm, a greenhouse, a tunnel or a train station.

17. A method according to claim 1, wherein the reduction of the biological contamination comprises the reduction of the level of viruses in the indoor air.

18. A method according to claim 1, which further comprises periodically or continuously measuring the Redox potential of the brine and adjusting the Redox potential of said brine based on the measured value of the Redox potential.

19. A method according to claim 18, wherein the Redox potential of the brine is increased by electrolyzing the brine.

20. A method according to claim 18, wherein the Redox potential of the brine is increased by enhancing the rate of flow of air flowing through the treatment zone.

21. A method according to claim 18, wherein the Redox potential of the brine is decreased by chemically treating the brine with one or more oxidizer-scavenging compounds.

22. A method according to claim 21, wherein the oxidizer-scavenging compound is a sulfur-based reducing agent selected from the group consisting of water soluble salts of sulfite, bisulfite, thiosulfate, metabisulfite, hydrosulfite and mixtures thereof.

* * * * *